(12) United States Patent
Bagherinia et al.

(10) Patent No.: US 10,832,402 B2
(45) Date of Patent: Nov. 10, 2020

(54) METHODS FOR DETECTION AND ENHANCED VISUALIZATION OF PATHOLOGIES IN A HUMAN EYE

(71) Applicant: Carl Zeiss Meditec, Inc., Dublin, CA (US)

(72) Inventors: Homayoun Bagherinia, Oakland, CA (US); Luis De Sisternes, San Francisco, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 252 days.

(21) Appl. No.: 15/891,965

(22) Filed: Feb. 8, 2018

(65) Prior Publication Data

US 2018/0260952 A1    Sep. 13, 2018

Related U.S. Application Data

(60) Provisional application No. 62/469,961, filed on Mar. 10, 2017.

(51) Int. Cl.
*G06K 9/00* (2006.01)
*G06T 7/00* (2017.01)
(Continued)

(52) U.S. Cl.
CPC .......... *G06T 7/0012* (2013.01); *A61B 3/0025* (2013.01); *A61B 3/102* (2013.01);
(Continued)

(58) Field of Classification Search
CPC ............. G06T 7/0012; G06T 7/10; G06T 2207/10101; G06T 2207/30041; A61B 3/0025; A61B 3/102
See application file for complete search history.

(56) References Cited

U.S. PATENT DOCUMENTS 7,301,644 B2   11/2007   Knighton et al.
8,332,016 B2   12/2012   Stetson
(Continued)

OTHER PUBLICATIONS

Bailey et al., "Detection of Occult Choroidal Neovascularization in Age-Related Macular Degeneration with Optical Coherence Tomography Angiography", Investigative Ophthalmology & Visual Science, vol. 56, Jun. 2015, p. 3329.
(Continued)

*Primary Examiner* — Shefali D Goradia

(74) *Attorney, Agent, or Firm* — Morrison & Foerster LLP

(57) ABSTRACT

Various methods for the detection and enhanced visualization of a particular structure or pathology of interest in a human eye are discussed in the present disclosure. An example method to visualize a given pathology (e.g., CNV) in an eye includes collecting optical coherence tomography (OCT) image data of the eye from an OCT system. The OCT image data is segmented to identify two or more retinal layer boundaries located in the eye. The two or more retinal layer boundaries are located at different depth locations in the eye. One of the identified layer boundaries is moved and reshaped to optimize visualization of the pathology located between the identified layer boundaries. The optimized visualization is displayed or stored or for a further analysis thereof.

7 Claims, 13 Drawing Sheets
(6 of 13 Drawing Sheet(s) Filed in Color)

(51) Int. Cl.
  *A61B 3/10*    (2006.01)
  *G06T 7/10*    (2017.01)
  *A61B 3/00*    (2006.01)
  *G06T 5/00*    (2006.01)

(52) U.S. Cl.
  CPC ............... *G06T 5/008* (2013.01); *G06T 7/10* (2017.01); *G06T 2207/10101* (2013.01); *G06T 2207/30041* (2013.01)

(56) References Cited

U.S. PATENT DOCUMENTS

| | | | |
|---|---|---|---|
| 8,571,278 | B2 | 10/2013 | Sonka et al. |
| 8,705,826 | B2* | 4/2014 | Liu .................... A61B 3/12 382/131 |
| 8,811,745 | B2 | 8/2014 | Farsiu et al. |
| 9,332,902 | B2 | 5/2016 | Tumlinson et al. |
| 10,123,698 | B2* | 11/2018 | Kotoku ............... A61B 3/0025 |
| 2015/0062590 | A1* | 3/2015 | Bagherinia ............ G06T 7/10 356/479 |
| 2016/0278627 | A1* | 9/2016 | Huang ................. A61B 3/0025 |
| 2016/0284085 | A1 | 9/2016 | Huang et al. |

OTHER PUBLICATIONS

Blazkiewicz et al., "Signal-To-Noise Ratio Study of Full-Field Fourier-Domain Optical Coherence Tomography", Applied Optics, vol. 44, No. 36, Dec. 20, 2005, pp. 7722-7729.

De Carlo et al., "Spectral-Domain Optical Coherence Tomography Angiography of Choroidal Neovascularization", American Academy of Ophthalmology, vol. 122, No. 6, 2015, pp. 1-11.

Efrat et al., "New Similarity Measures between Polylines with Applications to Morphing and Polygon Sweeping", Discrete & Computational Geometry, 2002, pp. OF1-OF35.

Fernandez et al., "Automated Detection of Retinal Layer Structures on Optical Coherence Tomography Images", Optics Express, vol. 13, No. 25, Dec. 12, 2005, pp. 10200-10216.

Gao et al., "Optical Coherence Tomography Angiography", Investigative Ophthalmology & Visual Science, vol. 57, No. 9, 2016, pp. OCT27-OCT36.

Gao et al., "Quantification of Choroidal Neovascularization Vessel Length Using Optical Coherence Tomography Angiography", Journal of Biomedical Optics, vol. 21, No. 7, Jul. 2016, pp. 076010-1-076010-8.

Garvin et al., "Intraretinal Layer Segmentation of Macular Optical Coherence Tomography Images Using Optimal 3-D Graph Search", IEEE Transactions on Medical Imaging, vol. 27, No. 10, Oct. 2008, pp. 1495-1505.

Harel et al., "Graph-Based Visual Saliency", Neural Information Processing Systems, vol. 1, No. 2, Dec. 2006, 8 pages.

Hillmann et al., "Holoscopy-Holographic Optical Coherence Tomography", Optics Letters, vol. 36, No. 13, Jul. 1, 2011, pp. 2390-2392.

Itti et al., "A Model of Saliency-Based Visual Attention for Rapid Scene Analysis", IEEE Transactions on Pattern Analysis and Machine Intelligence, vol. 20, No. 11, Nov. 1998, pp. 1254-1259.

Jia et al., "Quantitative Optical Coherence Tomography Angiography of Choroidal Neovascularization in Age-Related Macular Degeneration", American Academy of Ophthalmology, vol. 121, No. 7, Jul. 2014, pp. 1435-1444.

Liu et al., "Automated Choroidal Neovascularization Detection Algorithm for Optical Coherence Tomography Angiography", Biomedical Optics Express, vol. 6, No. 9, Sep. 1, 2015, pp. 3564-3575.

Lupidi et al., "Optical Coherence Tomography Angiography of a Choroidal Neovascularization in Adult Onset Foveomacular Vitelliform Dystrophy: Pearls and Pitfalls", Investigative Ophthalmology & Visual Science, vol. 56, No. 13, Dec. 2015, pp. 7638-7645.

Nakamura et al., "High-Speed Three-Dimensional Human Retinal Imaging by Line-Field Spectral Domain Optical Coherence Tomography", Optics Express, vol. 15, No. 12, Jun. 11, 2007, pp. 7103-7116.

Zhang et al., "Advanced Image Processing for Optical Coherence Tomographic Angiography of Macular Diseases", Biomedical Optics Express, vol. 6, No. 12, Dec. 1, 2015, pp. 4661-4675.

Zhang et al., "Minimizing Projection Artifacts for Accurate Presentation of Choroidal Neovascularization in OCT Micro-Angiography", Biomedical Optics Express, vol. 6, No. 10, Oct. 1, 2015, pp. 4130-4143.

* cited by examiner

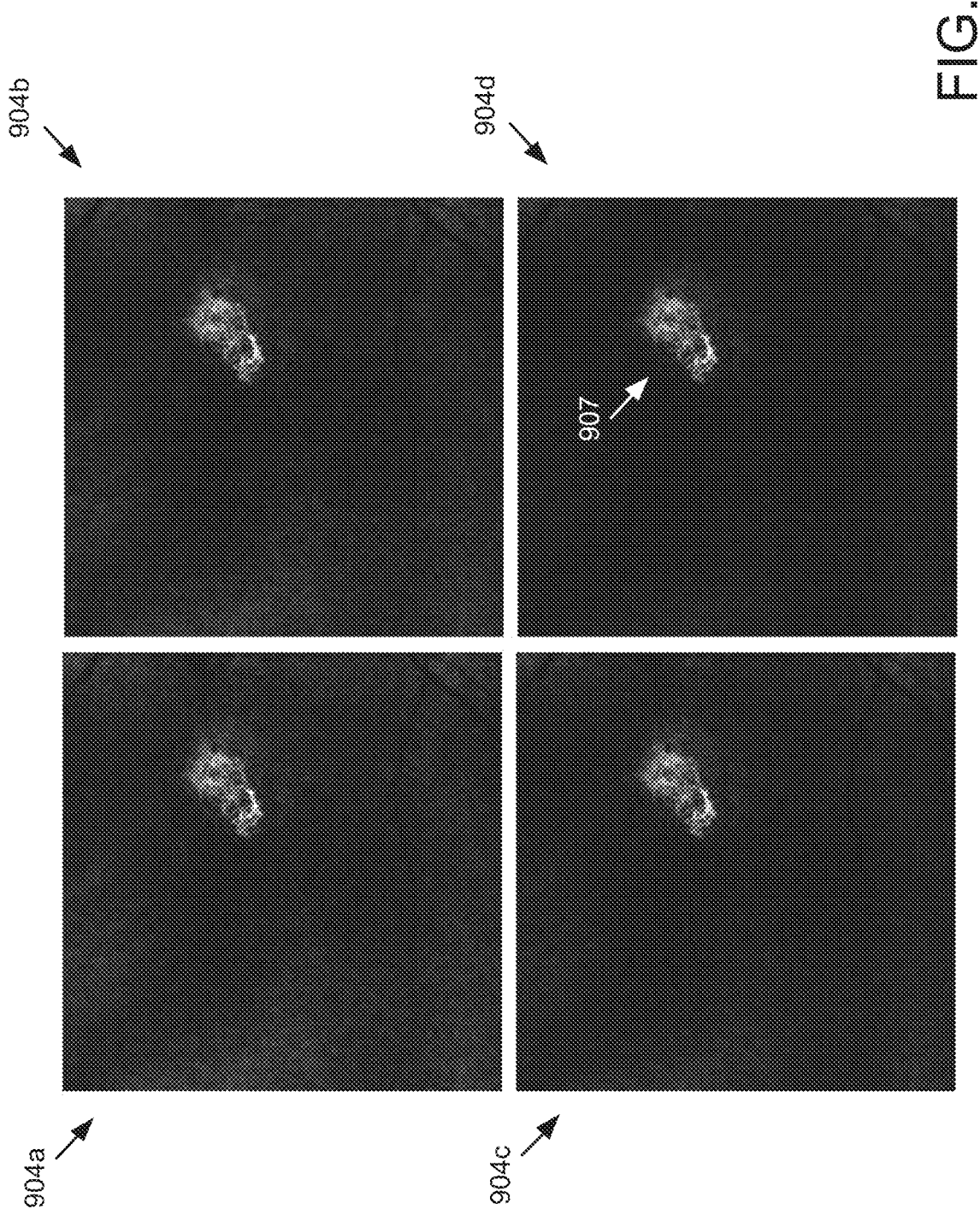

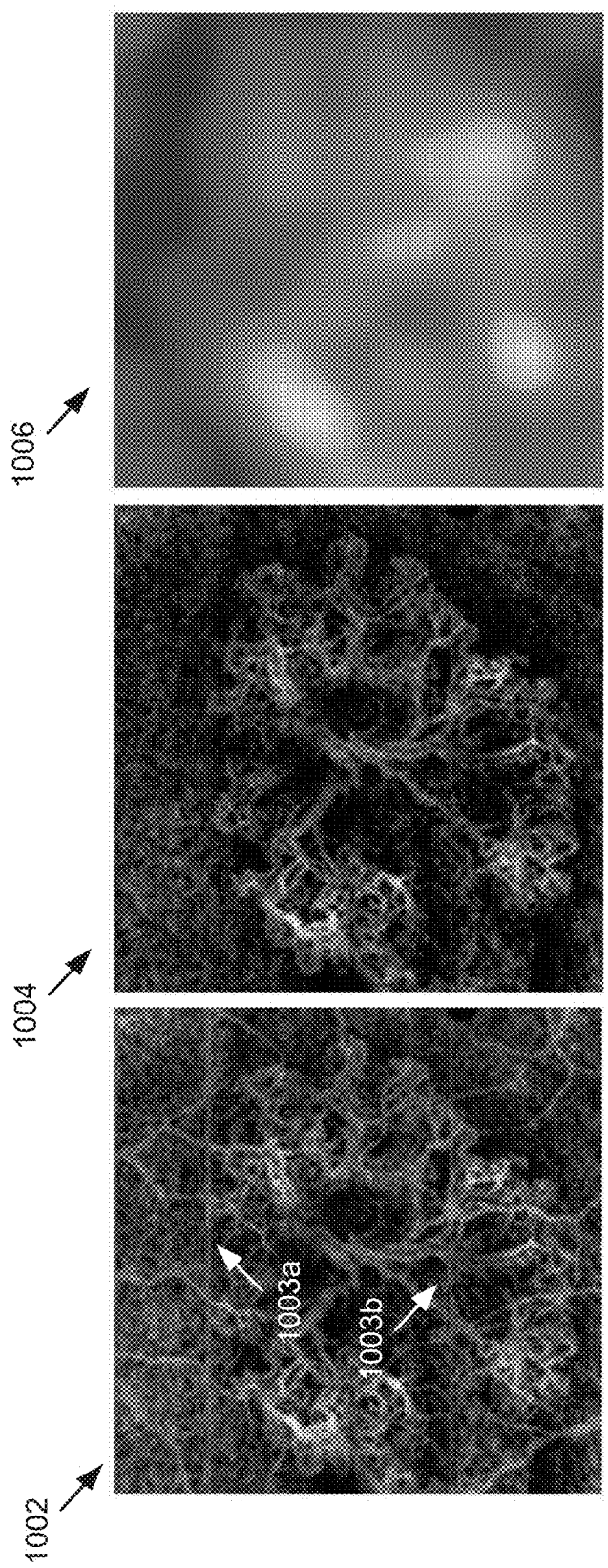

METHODS FOR DETECTION AND ENHANCED VISUALIZATION OF PATHOLOGIES IN A HUMAN EYE

PRIORITY

This application claims priority to U.S. Provisional Application Ser. No. 62/469,961 filed Mar. 10, 2017, the contents of which are hereby incorporated by reference.

BACKGROUND

Choroidal neovascularization (CNV) is an eye disease that involves growth of new blood vessels that originate from the choroid through a break in the Bruch's membrane into the sub-retinal pigment epithelium (sub-RPE) or sub-retinal space. See FIG. 3 for reference to different retinal layers and boundaries in a normal human eye. CNV can occur rapidly in individuals with defects in the Bruch's membrane, the innermost layer of the choroid. It can also occur as a result of a variety of ophthalmologic diseases, such as neovascular age-related macular degeneration (AMD), high myopia, central serous chorioretinopathy (CSCR), multifocal choroiditis, and others. Some of the symptoms that are associated with individuals suffering from CNV may include sudden deterioration of central vision, color disturbances, metamorphosia (distortions in which straight lines appear wavy), and feeling of pressure behind the eye.

One way of visualizing the CNV is through optical coherence tomography angiography (OCTA) (see for example, US Patent Publication No. 2016/0284085; Bailey, Steven T., et al. "Detection of occult choroidal neovascularization in age-related macular degeneration with optical coherence tomography angiography." *Investigative Ophthalmology & Visual Science* 56.7 (2015): 3329-3329; Talisa, E., et al. "Spectral-domain optical coherence tomography angiography of choroidal neovascularization." *Ophthalmology* 122.6 (2015): 1228-1238; Jia, Yali, et al. "Quantitative optical coherence tomography angiography of choroidal neovascularization in age-related macular degeneration." *Ophthalmology* 121.7 (2014): 1435-1444; Gao, Simon S., et al. "Quantification of choroidal neovascularization vessel length using optical coherence tomography angiography." *Journal of Biomedical Optics* 21.7 (2016): 076010-076010; Lupidi, Marco, et al. "Optical Coherence Tomography Angiography of a Choroidal Neovascularization in Adult Onset Foveomacular Vitelliform Dystrophy: Pearls and PitfallsOCT Angiography in AOFVD." *Investigative ophthalmology & visual science* 56.13 (2015): 7638-7645; each of which is hereby incorporated by reference).

To generate OCTA vasculature en face images for the visualization of a particular pathology, such as CNV, at least two retinal layer boundaries are required. One method involves manual segmentation where two layer boundaries are manually selected by a user and displaced together or independently up and/or down until a structure or pathology of interest that he/she is interested in is clearly visible. However, there are problems associated with this manual segmentation method. Some of them are that the method is time consuming and the shape of the two layer boundaries remain the same. Only the entire layer boundary is shifted axially. If there is a large error in the segmentation, then this procedure fails.

En face slabs can also be generated by identifying two or more retinal layer boundaries automatically by segmenting the OCT data using a multilayer segmentation algorithm (see for example, U.S. Pat. Nos. 8,571,278; 8,811,745; Garvin, M. K., et al. (2008). "Intraretinal layer segmentation of macular optical coherence tomography images using optimal 3-D graph search." IEEE Trans Med Imaging 27(10): 1495-1505; Cabrera Fernandez, D., et al. (2005). "Automated detection of retinal layer structures on optical coherence tomography images." Opt Express 13(25): 10200-10216, each of which is hereby incorporated by reference). In various eye disease cases, the position of a subset of retinal layer boundaries can be difficult to identify for a multilayer segmentation algorithm and/or an ophthalmologist/clinician. This may be because the boundaries are not distinguishable from each other and/or the boundaries are not visible in OCT images. This may also be due to not having enough information available to segment the OCT data automatically or interpret by a clinician correctly. Thus, the algorithm or the clinician would sometimes identify the wrong positions for a layer boundary.

Visualization of a particular structure or pathology of interest in the en face slabs generated using a multilayer segmentation algorithm is typically not optimal, since a given slab configuration defined a priori often excludes part of the signal of interest and includes other signals from nearby vascular structures. This results since such configurations are based on the segmentation of structure data and not optimized for the volumetric angiography signal. Automated segmentation of structure data often has errors and even when the structure information is correctly segmented, there is no guarantee that a particular vascular structure or pathology of interest will correspond to the same locations as indicated by the structural layers. Some pathologies are also very difficult to separate from other neighboring signals, for example, the separation of the CNV in AMD patients from neighboring choriocapillaris (CC) signal.

There have been some automated methods to enhance the slabs artificially through image processing for visualizing a pathology of interest (see for example, Zhang, Miao, et al. "Advanced image processing for optical coherence tomographic angiography of macular diseases." *Biomedical optics express* 6.12 (2015): 4661-4675), hereby incorporated by reference), but such methods merely work on the already generated slabs and do not solve the fundamental problem of isolating the signal of interest in three dimensions.

As mentioned earlier, CNV can be visualized with OCT angiography technology. However, it is important to address and resolve some problems associated with OCTA that can affect the quantification of CNV. Two significant problems include: 1) the occurrence of projection or decorrelation tail artifacts in the OCTA images, and 2) the presence of background signals due to choriocapillaris vessels and other unknown type of artifacts.

For the first problem, there have been various works done in the past for the artifacts removal/correction. One such work is presented by Ruikang K. Wang from University of Washington (see for example, Zhang, Anqi, Qinqin Zhang, and Ruikang K. Wang. "Minimizing projection artifacts for accurate presentation of choroidal neovascularization in OCT micro-angiography." *Biomedical optics express* 6.10 (2015): 4130-4143.). Problems with the artifact removal techniques in the previous methods is that they often remove signals which are associated with the pathologies that one wants to visualize (e.g., CNV vasculature pattern).

In regards to the second problem, the existing methods isolate the CNV by binarizing the angiography image (see for example, Liu, Li, et al. "Automated choroidal neovascularization detection algorithm for optical coherence tomography angiography." *Biomedical optics express* 6.9

(2015): 3564-3576., hereby incorporated by reference). The problem with binarization is that it may not be accurate around the CNV borders, which leads to inaccurate CNV measurement and quantification.

Therefore, what is needed are some new and improved methods that can overcome the limitations of the existing methods with respect to the detection and visualization of a particular structure or pathology of interest (e.g., CNV) as discussed above.

SUMMARY

According to one aspect of the subject matter described in the present application, a method for visualizing a pathology in an eye includes collecting optical coherence tomography (OCT) image data of the eye from an OCT system; segmenting the OCT image data to identify two or more retinal layer boundaries located in the eye; moving and reshaping one of the identified layer boundaries to optimize visualization of the pathology located between the identified layer boundaries; and displaying or storing the optimized visualization or a further analysis thereof.

According to another aspect of the subject matter described in the present application, a method for visualizing a pathology in an eye includes collecting three-dimensional optical coherence tomography (3D-OCT) image data of the eye from an OCT system; obtaining an initial slab from the 3D-OCT image data, the initial slab having a predefined upper limit and a predefined lower limit and containing the pathology within the upper and lower limits; generating a reference map based on the pathology to be visualized, said reference map being generated from the 3D-OCT image data and containing maximum values in the en face locations where the pathology is located and minimum values in other background en face regions; optimizing the upper and/or lower limits using the reference map for the visualization of the pathology; generating a final slab based on the optimized upper and lower limits, wherein the en face projection of the final slab clearly depicts the pathology; and displaying or storing the final slab or a further analysis thereof.

According to yet another aspect of the subject matter described in the present application, a method for visualizing a pathology in an eye includes collecting three dimensional optical coherence tomography (OCT) image data of the eye from an OCT system; calculating a motion contrast image from the OCT image data; generating a heat map of the image using an object detection method, said heat map representing point-wise weight values for pixels in the image, wherein one or more point-wise weight values for one or more image pixels corresponding to the pathology is higher than remaining pixels in the image; suppressing background features in the image using the heat map to enhance the visualization of the pathology; and displaying or storing the suppressed background image or a further analysis thereof.

The present invention is advantageous in a number of respects. For instance, the invention 1) can work with an initial/rough segmentation of the retinal layer boundaries and does not require a 100% accurate segmentation for the visualization of a pathology of interest (e.g., CNV), 2) allows the segmentation, quantification, and visualization of vessels, structures, and/or pathologies of interest in three dimensions, 3) generates an optimal en face slab for the visualization of a given vascular structure or pathology of interest, where subsequent manual adjustments or post-processing are not needed (or are minimal), 4) generates color-coded en face images where different pathologies or structures can be visualized in different colors, with the possibility to also encode depth of the pathologies or structures with different color shades, 5) the background suppression technique of the present invention preserves an object of interest borders for further analysis, and 6) uses multiple layers to achieve a high quality en face image with a clear depiction of a pathology by searching among possible en face images using mathematical optimization.

The features and advantages described herein are not all-inclusive and many additional features and advantages will be apparent to one of ordinary skill in the art in view of the figures and description. Moreover, it should be noted that the language used in the specification has been principally selected for readability and instructional purposes and not to limit the scope of the inventive subject matter.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 5A shows an example B-scan having an initial slab defined by upper and lower slab limits (shown with white lines) with superimposed red shading indicating angiography signal relating to the particular structure or pathology of interest and yellow arrows indicating compression in the upper and lower slab limits. FIG. 5B shows the resulting slab limits (whites lines) after the morphing technique.

FIG. 9B shows background suppressed images for four different degrees of background suppression.

FIG. 10A is another example illustration of a slab below RPE where CNV can be clearly visualized based on background suppression using a heat map. Similar to FIG. 9A, the left image is the original slab, the second image is the slab after projection artifact(s) removed, and the third image represents the corresponding heat map.

DETAILED DESCRIPTION

All patent and non-patent references cited within this specification are herein incorporated by reference in their entirety to the same extent as if the disclosure of each individual patent and non-patent reference was specifically and individually indicated to be incorporated by reference in its entirety.

Example OCT System

Figure 1:
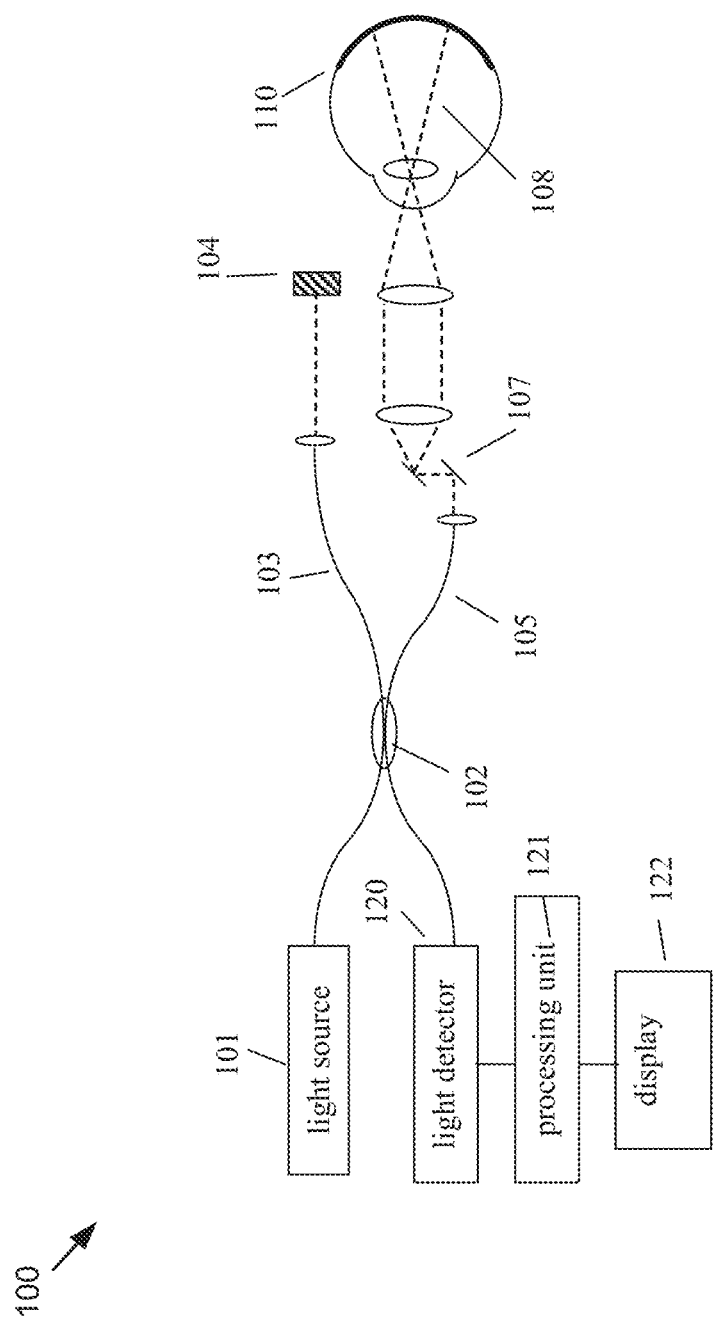
FIG. 1 is an illustration of a generalized optical coherence tomography (OCT) system that can be used to practice the present invention.

A generalized FD-OCT system used to collect 3-D image data of the eye suitable for use with the present invention is illustrated in FIG. 1. An FD-OCT system 100 includes a light source, 101, typical sources including but not limited to broadband light sources with short temporal coherence lengths or swept laser sources. A beam of light from source 101 is routed, typically by optical fiber 105, to illuminate the sample 110, a typical sample being tissues in the human eye. The source 101 can be either a broadband light source with short temporal coherence length in the case of SD-OCT or a wavelength tunable laser source in the case of SS-OCT. The light is scanned, typically with a scanner 107 between the output of the fiber and the sample, so that the beam of light (dashed line 108) is scanned laterally (e.g., in x and y) over the region of the sample to be imaged. Light scattered from the sample is collected, typically into the same fiber 105 used to route the light for illumination. Reference light derived from the same source 101 travels a separate path, in this case involving fiber 103 and retro-reflector 104 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 102, to form light interference in a detector 120. Although a single fiber port is shown going to the detector, those skilled in the art recognize that various designs of interferometers can be used for balanced or unbalanced detection of the interference signal. The output from the detector 120 is supplied to a processor 121 that converts the observed interference into depth information of the sample. The results can be stored in the processor 121 or other storage medium or displayed on display 122. The processing and storing functions may be localized within the OCT instrument or functions may be performed on an external processing unit (e.g., the computer system 1100 shown in FIG. 11) to which the collected data is transferred. This unit could be dedicated to data processing or perform other tasks which are quite general and not dedicated to the OCT device. The processor 121 may contain for example a field-programmable gate array (FPGA), a digital signal processor (DSP), an application specific integrated circuit (ASIC), a graphics processing unit (GPU), a system on chip (SoC) or a combination thereof, that performs some, or the entire data processing steps, prior to passing on to the host processor or in a parallelized fashion.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. Instead of mechanically scanning the beam, a field of light can illuminate a one or two-dimensional area of the retina to generate the OCT data (see for example, U.S. Pat. No. 9,332,902; D. Hillmann et al, "Holoscopy—holographic optical coherence tomography" *Optics Letters* 36(13): 2390 2011; Y. Nakamura, et al, "High-Speed three dimensional human retinal imaging by line field spectral domain optical coherence tomography" *Optics Express* 15(12): 7103 2007; Blazkiewicz et al, "Signal-to-noise ratio study of full-field Fourier-domain optical coherence tomography" *Applied Optics* 44(36): 7722 (2005)). In time-domain systems, the reference arm may have a tunable optical delay to generate interference. Balanced detection systems are typically used in TD-OCT and SS-OCT systems, while spectrometers are used at the detection port for SD-OCT systems. The invention described herein could be applied to any type of OCT system.

In Fourier Domain optical coherence tomography (FD-OCT), each measurement is the real-valued spectral interferogram ($S_j(k)$). The real-valued spectral data typically goes through several postprocessing steps including background subtraction, dispersion correction, etc. The Fourier transform of the processed interferogram, results in a complex valued OCT signal output $A_j(z)=|A_j|e^{i\varphi}$. The absolute value of this complex OCT signal, $|A_j|$, reveals the profile of scattering intensities at different path lengths, and therefore scattering as a function of depth (z-direction) in the sample. Similarly, the phase, $\varphi_j$ can also be extracted from the complex valued OCT signal. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. We use the term "cluster scan" herein to refer to a single unit or block of data generated by repeated acquisitions at the same location for the purposes of analyzing motion contrast. A cluster scan can consist of multiple A-scans or B-scans collected with relatively short time separations at approximately the same location(s) on the sample. A variety of ways to create B-scans are known to those skilled in the art including but not limited to along the horizontal or x-direction, along the vertical or y-direction, along the diagonal of x and y, or in a circular or spiral pattern. The majority of the examples discussed herein refer to B-scans in the x-z dimensions but the invention would apply equally to any cross sectional image.

The OCT system may use any one of a number of OCT Angiography processing algorithms on one or more cluster scans of OCT data collected at the same or approximately the same transverse locations on a sample at different times (see for example, Zhang, Anqi, Qinqin Zhang, and Ruikang K. Wang. "Minimizing projection artifacts for accurate presentation of choroidal neovascularization in OCT microangiography." Biomedical optics express 6.10 (2015): 4130-4143). As previously mentioned, motion contrast algorithms can be applied to the intensity information derived from the image data (intensity-based algorithm), the phase information from the image data (phase-based algorithm), or the complex image data (complex-based algorithm). An en face vasculature image is an image displaying motion contrast signal in which the data dimension corresponding to depth is displayed as a single representative value, typically by summing or integrating all or an isolated portion of the data.

The OCT system discussed herein may provide 2D (i.e. cross-sectional) images, en face images, 3-D images, metrics related to a health condition, and the like. This system may be used with any other system. For example, the OCT system may be used with a surgical system or surgical microscope system for diagnostic or treatment purposes. The OCT system may be used to analyze any sample. For example, the OCT system may be used in analysis, e.g. formation of images, of, for example, any type of life forms and inanimate objects. Examples of life forms may be animals, plants, cells or the like.

Detection and Quantification of Pathology of Interest

High Quality En Face Image Generation using Morphing of layer boundaries Continuously morphing or deforming a surface (1-D or 2-D) into another surface is important in computer graphics and computer vision. Some morphing examples may include special effects in motion pictures and animations that change one image or shape into another through a seamless transition (see for example, Har-Peled, Sariel. "New similarity measures between polylines with applications to morphing and polygon sweeping." *Discrete & Computational Geometry* 28.4 (2002): 535-569).

The concept of morphing can be applied to OCT image data for generating a high quality OCT en face image, which can be used for the visualization of a particular pathology, such as CNV. The high quality en face image generated using the morphing does not depend on correct segmentation of the retinal layer boundaries. Basically the best en face image depicting the particular pathology is calculated within a morphing process, as discussed in detail below with respect to FIG. 2.

Figure 2:
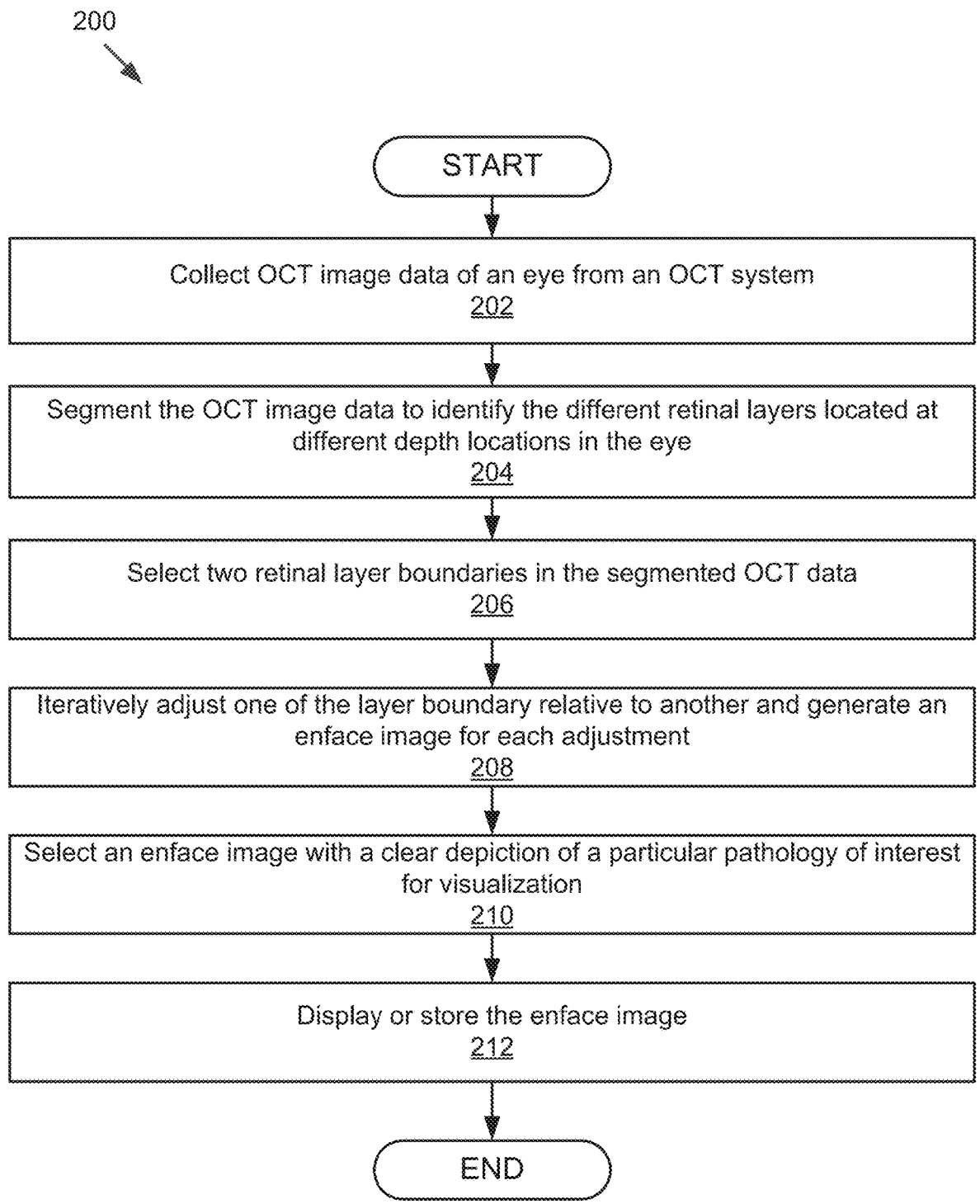
FIG. 2 is a flowchart of an example method for generating an en face image having a clear depiction of a particular pathology of interest (e.g., CNV) according to one aspect of the present invention.

FIG. 2 is a flowchart of an example method 200 for generating an en face image having a clear depiction of a particular pathology of interest according to one aspect of the present invention. It should be understood that the method 200 is not limited to the steps and/or operations embodied by this method and that other steps and/or operations are also possible and are within the scope of the present disclosure. The method 200 begins by collecting three-dimensional OCT image data of the eye from an OCT system (step 202), such as the OCT system 100 shown in FIG. 1. The three-dimensional OCT image data may include multiple B-scans taken at each location on a particular region of the eye. The method 200 may calculate motion contrast information in the three-dimensional OCT image data using an OCT angiography (OCTA) processing technique to obtain OCTA image data. The OCTA processing technique may include, without limitation, an intensity-based processing technique, a phase-based processing technique, a combination of the intensity-based and phase-based techniques, and a complex-based processing technique.

Figure 3:
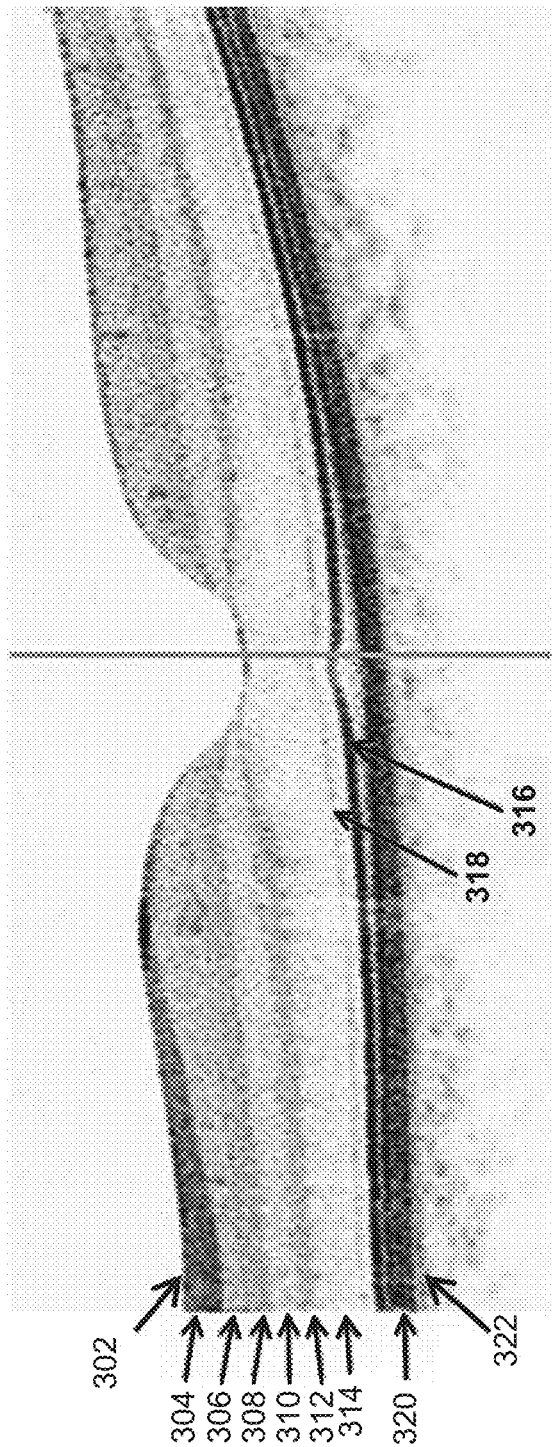
FIG. 3 is an OCT B-scan image of a normal retina of a human eye. The OCT image shows various canonical retinal layers and boundaries.

Next, in step 204, the method 200 segments the OCT and/or OCTA image data to identify different retinal layers located at different depth locations in the eye. The segmentation does not need to be very accurate since the method 200 is capable of performing its operation with rough or initial layer boundaries segmentation. FIG. 3 illustrates an OCT B-scan image representing various canonical retinal layers and boundaries, which includes, from top to bottom, the inner limiting membrane (ILM) 302, the retinal nerve fiber layer (RNFL or NFL) 304, the ganglion cell layer (GCL) 306, the inner plexiform layer (IPL) 308, the inner nuclear layer (INL) 310, the outer plexiform layer (OPL) 312, the outer nuclear layer (ONL) 314, the junction between the outer segments (OS) and inner segments (IS) (indicated by reference numeral 316) of the photoreceptors, the external or outer limiting membrane (ELM or OLM) 318, the retinal pigment epithelium (RPE) 320, and Bruch's membrane (BM) 322.

In step 206, the method 200 selects two layer boundaries or upper and lower surfaces from the segmented OCT data. In some embodiments, selection of the two boundaries/surfaces depends on the application (e.g., the target pathology or tissue type being studied/imaged/visualized) and/or disease type (e.g., type of disease being diagnosed/investigated/visualized). The application and/or disease type may be associated with the pathology being visualized. In some embodiments, the centroid surface that divides the OCT volume in the inner and outer retina could serve as upper and lower surfaces. It should be noted that multiple pairs of layer boundaries can be used to search for the desired en face image. Next, the method 200 iteratively adjusts (e.g., moves and reshapes) one of the layer boundaries relative to the other and generates an en face image based on the adjustment made in each iteration (step 208). The method 200 selects an en face image that has the best and clearest depiction of a particular pathology of interest (e.g., CNV) (step 210). In some instances, the method 200 performs the step 210 by analyzing each en face image generated during the morphing (i.e., step 208) and automatically stopping the iterative process when an en face image with quality meeting sufficient criteria (e.g., contrast, brightness, background features suppressed/removed, noise signals reduced, etc.) is found, as discussed in further detail below with respect to the mathematical equations. In some embodiments, the steps 206-210 are performed by the pathology visualizer 1105 (see FIG. 11) of the computer system 1100. The last step 212 of the method 200 involves displaying the selected en face image to a user on a display, such as the display 122 and/or storing the en face image in the memory of the system (e.g., memory 1104 of computer system 1100) for later analysis.

Figure 4:
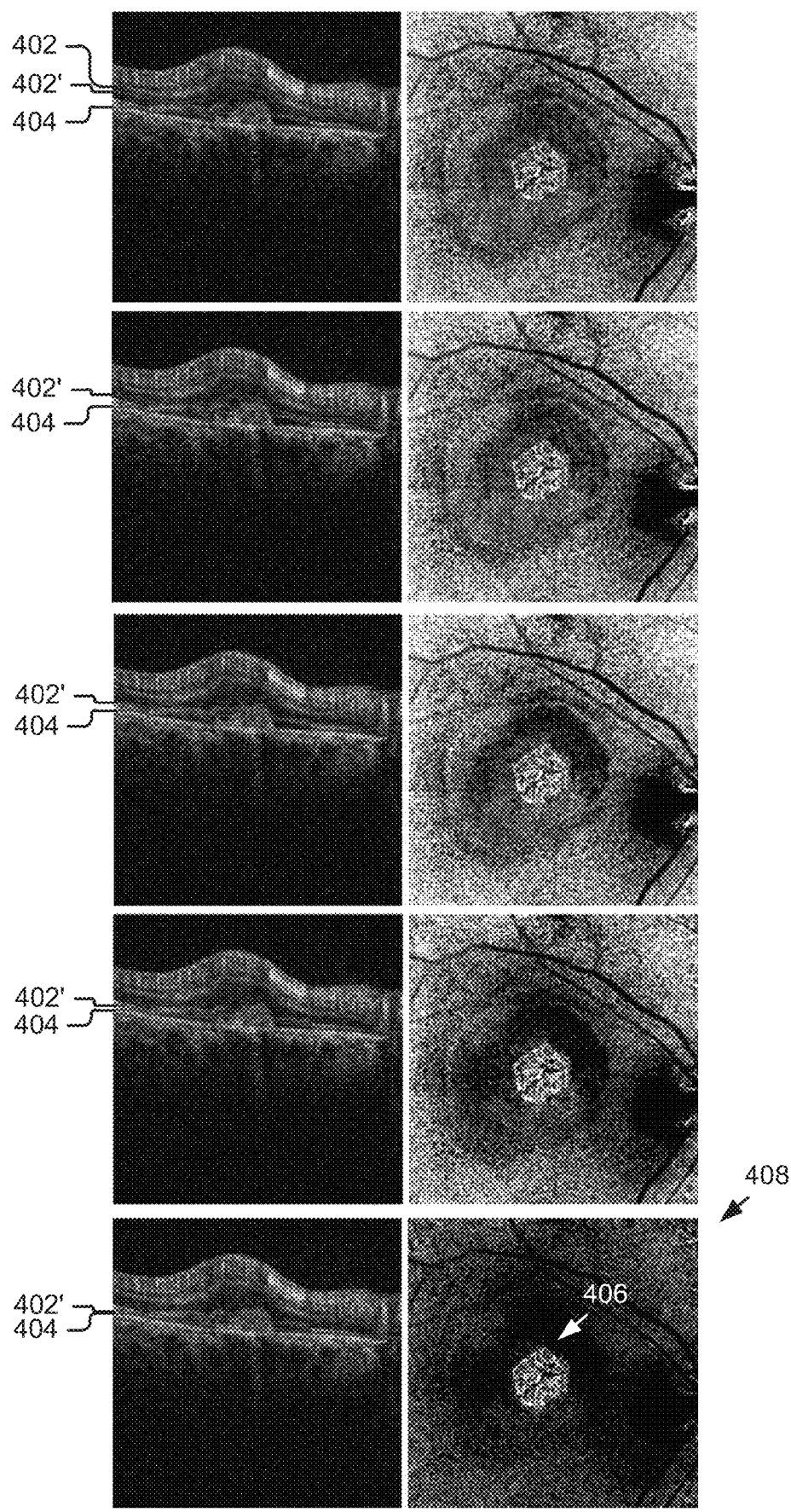
FIG. 4 shows an example morphing process for generating en face images for the visualization of choroidal neovascularization (CNV).

The steps 206, 208, and 210 of the method 200 can be more clearly visualized in reference to FIG. 4. The left images represent the morphing process between the OPL surface (indicated by reference numeral 402) and the RPE surface (indicated by reference surface 404), i.e., the OPL surface is moved towards the RPE surface for the visualization of CNV. This morphing process or movement of the OPL surface towards the RPE is indicated by reference numeral 402'. The images on right in FIG. 4 represent angiographic en face images that are generated during this morphing process. As depicted, the CNV 406 is clearly visible and the background signals reduced in the en face image 408 generated in the 5$^{th}$ iteration.

In some embodiments, generating an en face image with the best depiction of a given pathology can be formulated as a mathematical optimization problem. As discussed above, the best en face image is found within a morphing process. Each intermediate step of the morphing process generates an en face image. We stop the morphing process when an en face image with the highest quality is generated (e.g., no further improvement is achieved with continued morphing, or an achieved quantified quality is within a predefined range). Mathematically this process can be formulated as follows:

$$\max_{h_i} f(E(g, h_i))$$

or $$\min_{h_i} f(E(g, h_i))$$

where $f$ is the objective function ($f:R^n \to R$), E is the en face image, h is an intermediate surface (deformed surface) into surface g. g could be the top $l_t$ or the bottom $l_b$ layer boundary.

h can be generated by sophisticated morphing algorithm as known in the literatures. A simple method is described by the following equations:

$$h_i = l_t + \alpha_i(l_b - l_t)$$

where $\alpha_i \in [0,1]$ is the weight.

An example for $f$ could be $$f = \Sigma \nabla E$$

where $\nabla$ represents the en face image gradient. En face image E can be generated by integral (or other methods) of a sub OCT volume between two layers h and g.

Slab Optimization Based on Morphing for Visualizing Pathology

Figure 5B:
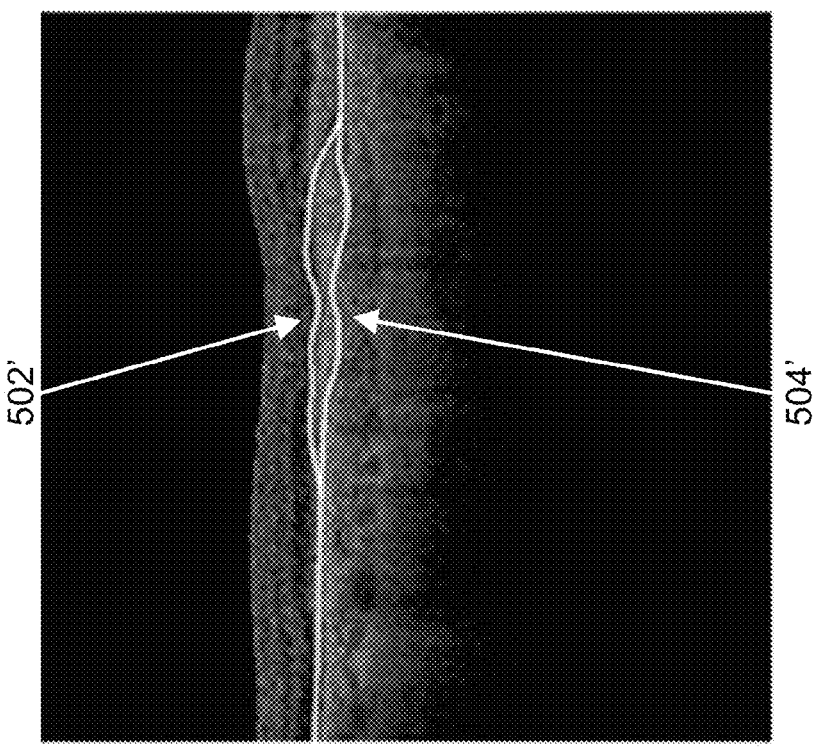
FIGS. 5A and 5B illustrate an example slab optimization technique for the visualization of a particular pathology of interest based on a morphing technique. In particular.
Figure 5A:
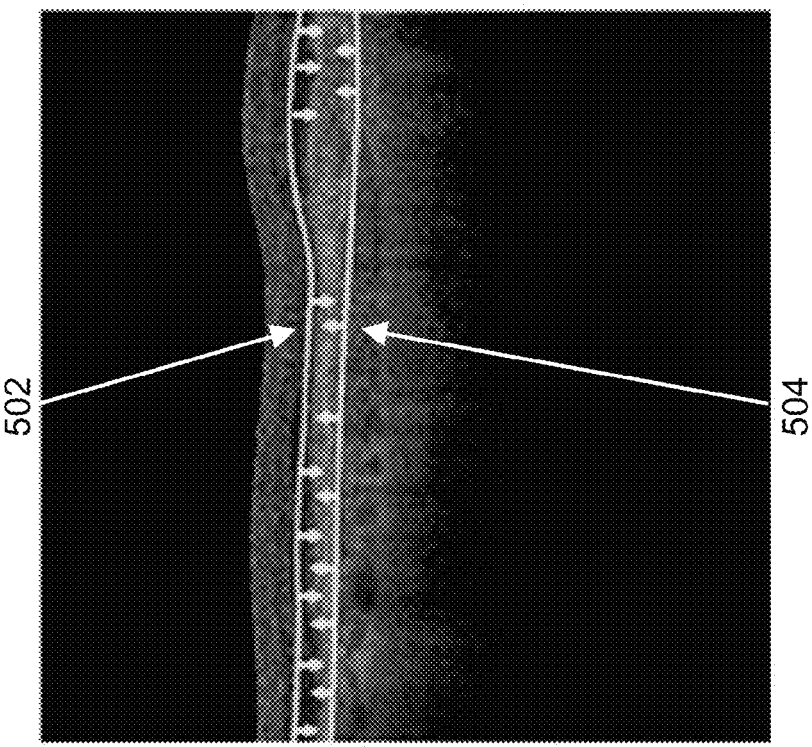

The morphing process as discussed above could also be applied to automatically create an optimal slab in a three dimensional OCT angiography (3D OCTA) data set to visualize a particular structure or pathology of interest, such as CNV, on a scan-by-scan basis. The main idea of the slab optimization method consists of morphing of the slab limits (upper and lower limits of a slab within the 3D OCTA data) in an iterative manner so that it converges into those that optimize the visualization of the vascular signal of interest, while reducing its thickness in background regions to zero (or very low values). An example of the main concept of this slab optimization method is illustrated with respect to FIGS. 5A and 5B. In particular, FIG. 5A shows an example B-scan having an initial slab defined within the upper and lower slab limits (shown with white lines 502 and 504) with superimposed red shading indicating angiography signal relating to the particular structure or pathology of interest and yellow arrows indicating compression in the upper and lower slab limits. FIG. 5B shows the resulting slab limits (indicated by reference numerals 502' and 504') after the morphing process discussed herein (for example, with respect to method 600 in FIG. 6). Note that although a singular B-scan is shown as an example, the process takes advantage of three-dimensional information and the axial location of the slab limits are defined to evolve within the horizontal/vertical plane.

Figure 6:
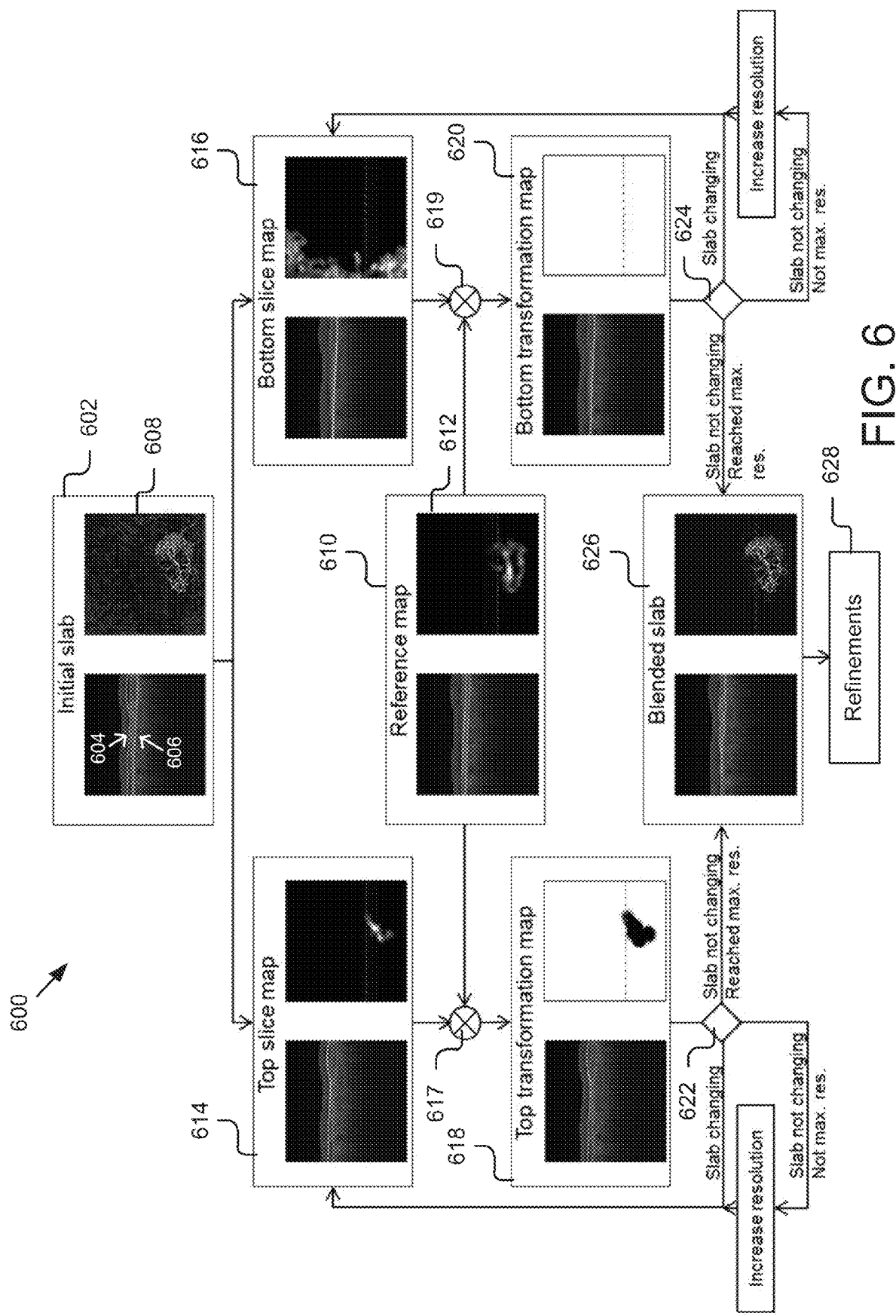
FIG. 6 is a flowchart of an example slab optimization method according to one aspect of the present invention.

The slab optimization is now described with respect to the method 600 in FIG. 6. It should be noted that although the method 600, in particular, describes the slab optimization for the visualization of CNV, the main idea behind this method could be employed to optimize the visualization of other retinal vascular structures or pathologies as well. It should also be noted that while the method 600 is outlined on OCTA data, the method could also apply to OCT structural data. The method is case-adaptive, meaning that the slab limits are automatically adapted to each case and the possible vascular structure or pathologies that one wants to visualize. The result from this method is the volumetric segmentation of the particular pathology or vascular structure of interest within the OCTA volume in the form of upper and lower slab limits. The result could be further processed by additional methods to generate a more precise segmentation of the pathology or vascular structure of interest where holes within the overall volume can be present.

In step 602, an initial slab is originally defined to contain the volumetric vascular structure of interest within its upper and lower limits, in this case the CNV signal. The upper and lower limits (indicated by reference numerals 604 and 606) will be evolved in the consecutive steps. The definition of the initial slab is set a priori depending on the vascular signal one wants to visualize and it can be based on the volumetric segmentation of the structure information in an OCTA scan. Since the location of the vascular structure or pathology of interest is not known a priori from the layered structure of the retina, this slab is defined so that it contains the signal of interest (indicated by red dots within 604 and 606) while also containing other possible background signal, making the goal of the method to isolate the desired angiography signal from background signal. For example, for the visualization of CNV, since we know CNV are located somewhere within the outer retina and Bruch's membrane, the initial slab could be defined with an upper limit describing the location of the outer plexiform layer (OPL) and a lower limit describing the location of Bruch's membrane plus an offset, both locations obtained by an automated or semi-automated segmentation of the structure data. Reference numeral 608 shows an en face projection of the initial slab.

In step 610, a reference map is generated from the same OCT data (i.e., from which the initial slab was obtained) in which the location of the CNV in the horizontal/vertical plane (en face plane) is roughly highlighted, as shown in the en face projection 612. The goal of this reference map is to have maximum values in the en face locations where the vascular signal of interest is located and minimum values in other background en face regions. For example, in the particular case of CNV visualization, this reference map can be generated by considering the sum and/or maximum en face projection of the angiography signal located within ±50 microns of Bruch's membrane. Further processing can then be applied to remove possible superficial vessels from the image and to increase the intensity of the vasculature patterns observed in CNV over background choriocapillaris (CC) signal. This processing can be done using several image processing methods like morphological operations and filtering, for example, Hessian, Frangi, Gabor or saliency filters.

In some embodiments, the reference map can also be generated by an initial morphing of the slab limits from top to bottom or vs. using weighted averaging of the slab limits. The weight that maximizes the local contrast/energy of a reference map is selected as the solution. Other alternative methods to weighted averaging can also be considered to find a reference map.

In steps 614 and 616, top and bottom slice maps are respectively generated by considering the angiography signal in the vicinity of the evolving upper and lower slab limits at each iteration step. The top slice map is an en face image (step 614) that can be generated by projecting axially (either using a maximum or sum projection method) the angiography signal located at increasing axial depths within a given limit from the evolving upper slab. We call this given axial limit the thickness of the top slice map ($T_T$). The bottom slice map (step 616) is an en face image that can be generated by projecting axially (either using a maximum or sum projection method, see for example U.S. Pat. Nos. 7,301,644 and 8,332,016) the angiography signal located at decreasing axial depths within a given limit from the evolving lower slab. We call this second given axial limit the thickness of the bottom slice map ($T_B$). Both the resulting projected maps can also be further processed by similar image processing methods as discussed with respect to reference map generation (step 610) for maximizing the visualization of the vascular signal of interest.

In steps 618 and 620, top and bottom transformation maps are generated by assessing the similarity of the top and bottom slice maps with the reference map, respectively (as indicated by reference numerals 617 and 619). The top and bottom transformation maps indicate the number of pixels that the evolving upper and lower limits are displaced at each en face position in a particular iteration step, respectively. These transformation maps are inversely proportional to the corresponding similarities of the top and bottom slice maps with the reference map, i.e., en face regions of high similarity will have a lower displacement while dissimilar regions will have a more pronounced displacement, in order to stop the evolution in those locations where the signal of interest is found and continue the slab compression in those locations where no signal of interest is found.

A comparison of the reference map with each of the slice maps can be made using an en face map (similarity map) and can be computed by a number of methods, such as for example, pixel-by-pixel multiplication, analysis of cross-correlation between both images, analysis of structural similarity (SSIM) maps between both images, etc. These similarity maps will have high values in similar regions and lower values in dissimilar regions between both maps. The transformation maps are generated by inverting this effect, taking lower values in regions with high similarity and lower values in regions with high similarity. Both the top and bottom transformation maps are then scaled to have a value of 0 in the regions of highest similarity and a maximum displacement value ($D_T$ and $D_B$ for the top and bottom transformation maps, respectively) in the regions of lowest similarity or low values of the corresponding slice maps (low angiography signal). The transformation maps can be later post-processed by several morphological operations and filtering in a similar manner as previously indicated to ensure smoothness in the transformations. Additionally, a cumulative transformation map (considering the accumulation of transformations applied to the upper and lower slab limits throughout the iterative process) can also be considered and post-processed to improve smoothness of the overall transformations applied to the evolving slab limits.

Next, in steps 622 and 624, a determination is made as to whether the top and bottom transformation maps indicate a change in displacement in the upper and lower limits, respectively. If the result of the determination is displacement change, then steps 614-617-618-622 and/or steps 616-619-620-624 are repeated until the upper limit and/or the lower limit are evolved to an axial depth where the particular vascular structure of pathology of interest is located. The compression of the slab limits in each iteration are governed by assessing the similarities between the reference map and top and bottom slice maps generated from thin slabs defined within the evolving upper and lower limits at each iterative step, respectively. This way, the upper and lower evolving limits of the slab are transformed so that their evolution stops at the axial depth where the particular pathology of interest (e.g., CNV) is located and the resulting slab thickness is minimized in en face locations where the signal of interest is not present.

The morphing process discussed herein with respect to method 600 can also be repeated in a series of consecutive steps with increasing resolution. That is, the slab limits are first evolved using a downsampled or interpolated version of the OCTA flow volume at a lower resolution, and the resulting optimized slab limits are further processed in consecutive steps using versions of increased resolution. Note that in the displayed method 600, the evolution of the upper and lower slab limits are shown as two independent iterative processes, but this method could also be adapted to encompass information from both limits to describe the transformation maps at each step in the iteration. Also note that the method could also be adapted without a reference map, with the goal of optimizing a slab to increase the visualization of any vessel-like structure included within the original initial slab limits.

When the iterative process stops and all the possible resolution instances have been completed (e.g., no change in the slab is produced with new iteration(s) and/or a (predefined) maximum resolution is reached), in step 626, the resulting evolved upper and lower limits are assigned as the limits of the resulting blended slab. The iterative transformation of the top and bottom limits in an independent process could result in en face regions where the axial depth of the upper limit is greater than the lower limit, associated with the lack of any signal of interest in such regions. Such regions can be removed from the slab definition or can be assigned a given baseline depth value for both the upper and lower limits, resulting in zero-pixel thickness.

The above discussed method 600 can be followed by one or more optional refinement steps 628 to further improve the quality of the resulting slab, to eliminate false positive volumetric regions from the resulting slab, and/or to add neighboring volumetric regions with signal of interest to the slab limits. These refinements are oriented to enhance the accuracy of the slab limits (minimizing volumetric regions within the slab limits that do not correspond to the vascular structure or pathology of interest while also maintaining the regions of interest not included between the slabs limits at a minimum) and could be achieved by further processing the slab limits using image processing, both considering or not considering the intensity and/or angiography data recorded throughout the cube. In the same manner, additional post-processing can also be considered to produce a more precise segmentation of the vessels from pathology or structure of interest where holes within the overall volume can be present.

In some embodiments, the resulting evolved slab can be used to generate color-coded en face images where the structure or pathology of interest isolated by the evolved slab can be visualized in a different color with respect to other retina vessels, as shown and discussed, for example, with respect to FIGS. 7A-D. These color-coded images can indicate the location of the pathology of interest within other retina vessels and/or encode the depth of the pathology within the retina using different color shading.

Figures 7A, 7B, 7C, 7D:
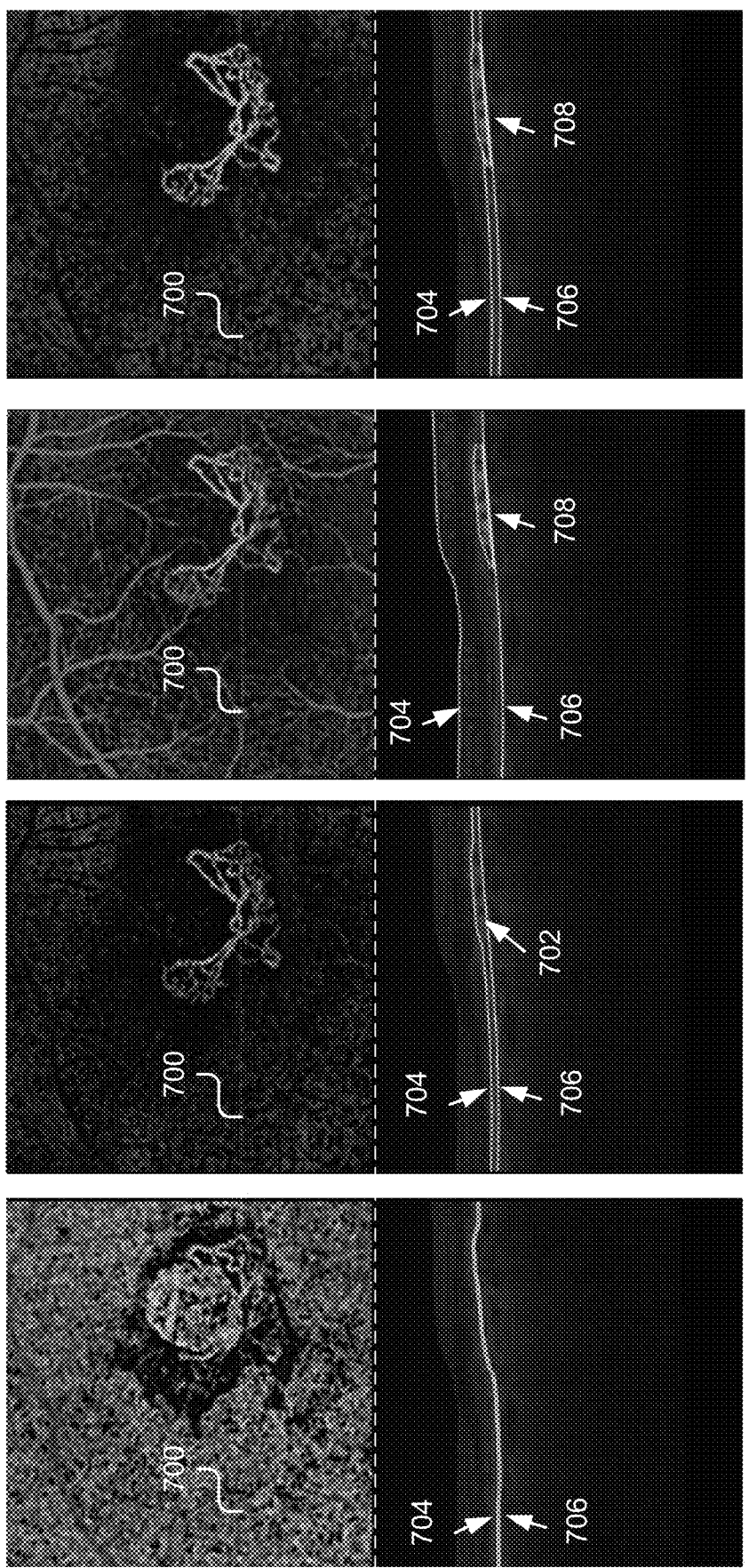
FIGS. 7A-7D illustrate exemplary color-coded en face images (top) and corresponding structure B-scans (underneath the en face images) for visualization of CNV in different colors with respect to other retina vessels.

FIGS. 7A-7D illustrate exemplary color-coded en face images (top) and corresponding structure B-scans (underneath the en face images) for visualization of CNV with respect to other retina vessels. In particular, the top images from left to right show: (1) an original choriocapillaris (CC) slab definition (FIG. 7A); (2) the slab produced by considering the result of the top evolved slab as upper limit and the bottom of an RPE-Fit+37 microns as lower limit (FIG. 7B); (3) a color-coded slab with normal retinal vessels in red, region of CNV vessels obtained by the slab optimization method (method 600 in FIG. 6) in green, and CC vessels in blue (FIG. 7C); and (4) a color-coded slab with the region of CNV vessels colored in red-to-green shades according to increasing depth within the retina and the CC vessels in blue (FIG. 7D). The image underneath each en face image displays the structure B-scan (located as indicated by the horizontal red line 700 in the en face images on top), with superimposed angiography signal in the same color as shown in the corresponding en face images (note that: for black and white en face images (such as the ones depicted in FIGS. 7A and 7B), the angiography signal is displayed with red shading in the B-scans (as indicated by reference numeral 702)). The white lines 704 and 706 in each B-scan indicate the corresponding slab limits (i.e., upper and lower limits) for its respective slab and the yellow regions (indicated by reference numeral 708) indicate the isolated CNV volume identified by the slab optimization method 600 described herein.

The slab optimization method discussed herein is automated for visualizing a predefined structure of interest (for example, CNVs) but it should be noted that the method can also be used in a semi-automated manner where a user defines a region of interest containing the vascular structure or pathology to visualize. Also note that the method could also be adapted without a reference map, with the goal of optimizing a slab to increase the visualization of any vessel-like structure included within the original initial slab limits.

Enhanced Visualization of the Pathology of Interest Using a Heat Map

In another embodiment of the present application, a particular structure or pathology of interest (e.g., CNV) can be visualized using a heat map. The basic idea is to generate a heat map indicating the probable location of CNVs or any object of interest in a homogenous background (e.g. choriocapillaris).

Figure 8:
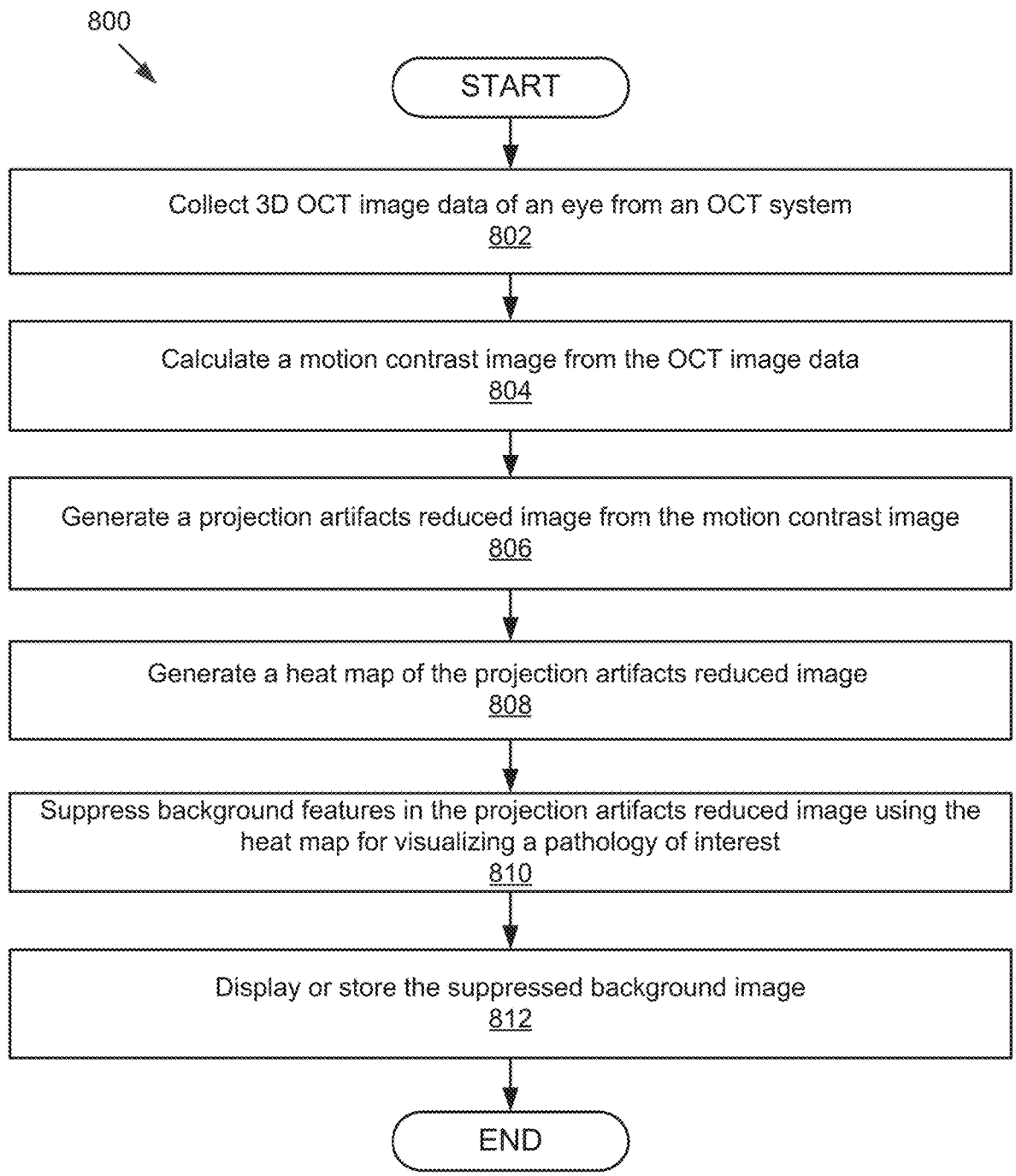
FIG. 8 is a flowchart of an example method for suppressing background signals from an OCT angiography (OCTA) image using a heat map for visualization of a particular pathology of interest.

FIG. 8 is a flowchart of an example method 800 for suppressing background signals from an OCTA image using a heat map for visualization of a particular pathology of interest. It should be understood that the method 800 is not limited to the steps and/or operations embodied by this method and that other steps and/or operations are also possible and are within the scope of the present disclosure. The method 800 begins by collecting three-dimensional OCT image data of the eye from an OCT system (step 802), such as the OCT system 100 shown in FIG. 1. The three-dimensional OCT image data may include multiple B-scans taken at each location on a particular region of the eye. The method 800 may calculate a motion contrast image (see for example, image 902 in FIG. 9A) from the three-dimensional OCT image data using an OCT angiography (OCTA) processing technique (step 804). The OCTA processing technique may include, without limitation, an intensity-based processing technique, a phase-based processing technique, a combination of the intensity-based and phase-based techniques, and a complex-based processing technique.

Figure 9A:
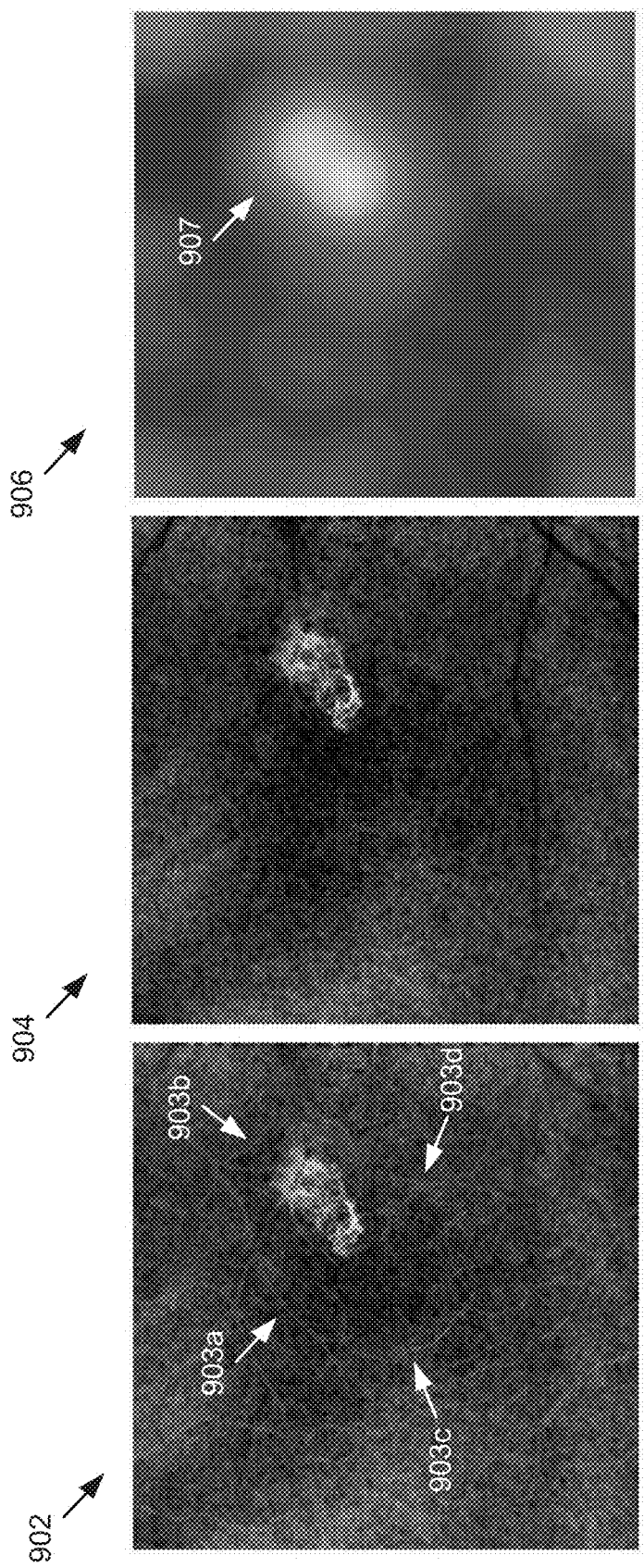
FIG. 9A shows an example of a slab below the RPE where CNV can be seen by suppressing the background signals/features using a heat map. The left image is the original slab, the second image is the slab after projection artifact(s) removed, and the third image represents the corresponding heat map. The location of the CNV is clearly shown in the heat map.

The motion contrast image generated in step 804 may contain projection artifacts, as shown for example by reference numerals 903a-d in FIG. 9A. In step 806, a projection artifacts reduced image is generated (see for example, image 904 in FIG. 9A) using a projection artifact reduction technique, such as techniques discussed in Zhang. Anqi, Qinqin Zhang, and Ruikang K. Wang. "Minimizing projection artifacts for accurate presentation of choroidal neovascularization in OCT micro-angiography." *Biomedical Optics Express* 6.10 (2015): 41:30-4143, and Jia, Yali, et al. "Quantitative optical coherence tomography angiography of choroidal neovascularization in age-related macular degeneration." *Ophthalmology* 121.7 (2014): 1435-1444.

Next, the method 800 generates a heat map of the projection artifacts reduced image (step 808). The generated heat map contains a location of the pathology of interest. One such heat map is shown in image 906 in FIG. 9A highlighting the location of the CNV (indicated by reference numeral 907). The heat map can be generated using an object detection algorithm called image saliency detection (see for example, Harel, J., Koch, C., & Perona, P. (2006, December). "Graph-based visual saliency." NIPS (Vol. 1, No. 2, p. 5) and Itti, L., Koch, C., & Niebur, E. (1998). "A model of saliency-based visual attention for rapid scene analysis." *IEEE Transactions on pattern analysis and machine intelligence*, 20(11), 1254-1259). The heat map can also be generated using various vessel detection methods including, for example, Frangi, phase congruency, Gabor-based methods, etc.

In step 810, the background features or signals in the projection artifact reduced image are suppressed using the heat map. The heat map can be used as a weight function to weigh the artifact reduced image containing the pathology (e.g., CNVs). Also the heat map can be used for point-wise transformation of the image where each heat map value represents the transformation parameter for each pixel in the image. Other methods can be considered to use the heat map to enhance the pathology visualization. By way of an example illustration, FIG. 9B shows background suppressed image 904a-d for four different degrees of background suppression upon weighting the projection artifacts reduced image 904 with the heat map 906. As depicted, the $4^{th}$ degree background suppressed image 904d has the minimal background features/signals with a clear visual of the CNV (indicated by reference numeral 907).

Figure 10B:
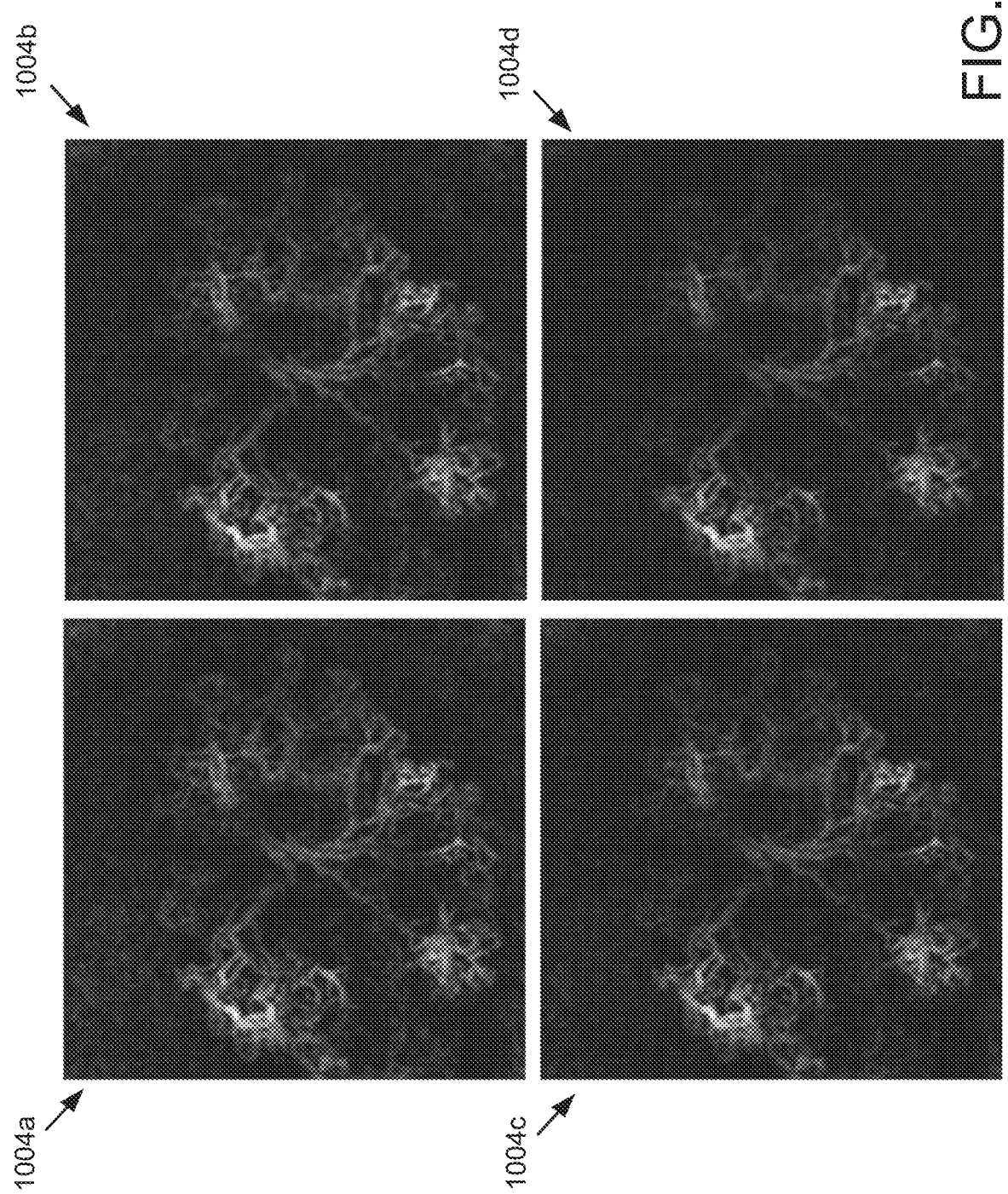
FIG. 10B shows results of four different degrees of background suppression.

Steps 804-810 are further discussed with respect to example illustrations in FIGS. 10A and 10B. In particular, FIG. 10A shows an example of a slab below the RPE where CNV can be seen by suppressing the background features using a heat map. The left image 1002 is the original slab image, the second image 1004 is the slab after projection artifacts (e.g., artifacts 1003a and 1003b) have been removed, and the third image 1006 represents the corresponding heat map. The location of the CNV is clearly shown in the heat map. The background of the second image 1004 can be suppressed by weighting the image with the heat map 1006 where the location of the CNV has more weight than the background. FIG. 10B shows four background suppressed images 1004a-d for four different degrees of background suppression.

The last step 812 of the method 800 involves displaying the suppressed background image to a user on a display, such as the display 122 and/or storing the image in the memory of the system (e.g., memory 1104 of computer system 1100) for later analysis.

Example Computer System

Figure 11:
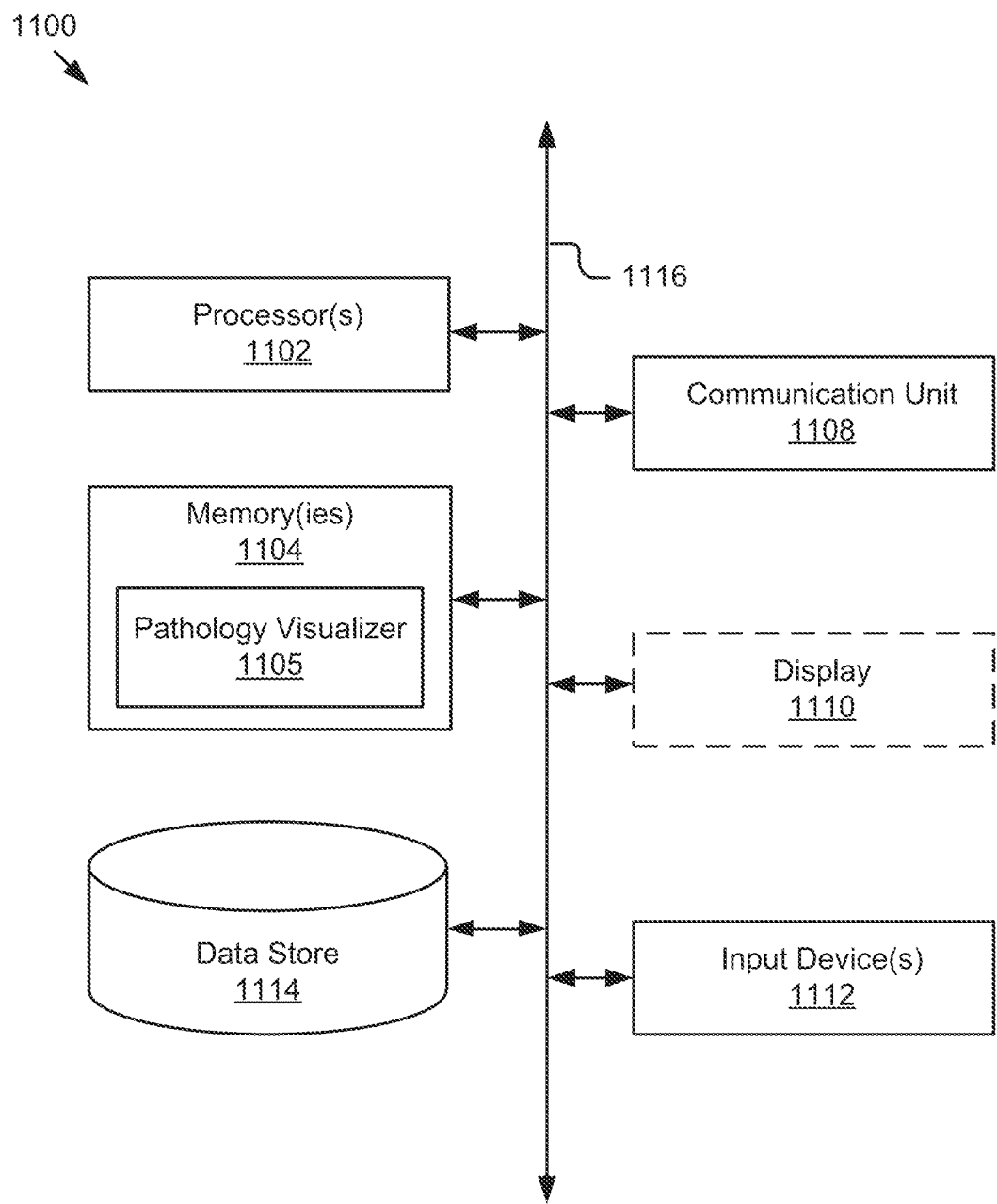
FIG. 11 is a block diagram of a general computer system that may perform the functions discussed in the disclosure according to one aspect of the present invention.

The processing unit or processor 121 that has been discussed herein in reference to FIG. 1 can be implemented with a computer system configured to detect and visualize a particular structure or pathology of interest in an eye. For instance, the processing unit 121 can be implemented with the computer system 1100, as shown in FIG. 11. The computer system 1100, as depicted, may include one or more processors 1102, one or more memories 1104, a communication unit 1108, an optional display 1110, one or more input devices 1112, and a data store 1114. The display 1110 is shown with dotted lines to indicate it is an optional component, which, in some instances, may not be a part of the computer system 1100. In some embodiments, the display 1110 discussed herein is the display 122 that has been discussed herein in reference to FIG. 1.

The components 1102, 1104, 1108, 1110, 1112, and 1114 are communicatively coupled via a communication or system bus 1116. The bus 1116 can include a conventional communication bus for transferring data between components of a computing device or between computing devices. It should be understood that the computing system 1100 described herein is not limited to these components and may include various operating systems, sensors, video processing components, input/output ports, user interface devices (e.g., keyboards, pointing devices, displays, microphones, sound reproduction systems, and/or touch screens), additional processors, and other physical configurations.

The processor(s) 1102 may execute various hardware and/or software logic, such as software instructions, by performing various input/output, logical, and/or mathematical operations. The processor(s) 1102 may have various computing architectures to process data signals including, for example, a complex instruction set computer (CISC) architecture, a reduced instruction set computer (RISC) architecture, and/or architecture implementing a combination of instruction sets. The processor(s) 1102 may be physical and/or virtual, and may include a single core or plurality of processing units and/or cores. In some embodiments, the processor(s) 1102 may be capable of generating and providing electronic display signals to a display device, such as the display 1110, supporting the display of images, capturing and transmitting images, performing complex tasks including various types of feature extraction and sampling, etc. In some embodiments, the processor(s) 1102 may be coupled to the memory(ies) 1104 via a data/communication bus to access data and instructions therefrom and store data therein. The bus 1116 may couple the processor(s) 1102 to the other components of the computer system 1100, for example, the memory(ies) 1104, the communication unit 1108, or the data store 1114.

The memory(ies) 1104 may store instructions and/or data that may be executed by the processor(s) 1102. In the depicted embodiment, the memory(ies) 1104 stores at least a pathology visualizer 1105, which may include software, code, logic, or routines for performing any and/or all of the techniques described herein. For instance, execution of the pathology visualizer 1105 may perform all or some of the steps discussed in reference to method 200 (FIG. 2), method 600 (FIG. 6), and method 800 (FIG. 8). In some embodiments, the memory(ies) 1104 may also be capable of storing other instructions and data including, for example, an operating system, hardware drivers, other software applications, databases, etc. The memory(ies) 1104 are coupled to the bus 1116 for communication with the processor(s) 1102 and other components of the computer system 1100. The memory(ies) 1104 may include a non-transitory computer-usable (e.g., readable, writeable, etc.) medium, which can be any apparatus or device that can contain, store, communicate, propagate or transport instructions, data, computer programs, software, code, routines, etc. for processing by or in connection with the processor(s) 1102. A non-transitory computer-usable storage medium may include any and/or all computer-usable storage media. In some embodiments, the memory(ies) 1104 may include volatile memory, non-volatile memory, or both. For example, the memory(ies) 1104 may include a dynamic random access memory (DRAM) device, a static random access memory (SRAM) device, flash memory, a hard disk drive, a floppy disk drive, a CD ROM device, a DVD ROM device, a DVD RAM device, a DVD RW device, a flash memory device, or any other mass storage device known for storing instructions on a more permanent basis.

The computer system 1100 may include one or more computers or processing units at the same or different locations. When at different locations, the computers may be configured to communicate with one another through a wired and/or wireless network communication system, such as the communication unit 1108. The communication unit 1108 may include network interface devices (I/F) for wired and wireless connectivity. For example, the communication unit 1108 may include a CAT-type interface, USB interface, or SD interface, transceivers for sending and receiving signals using Wi-Fi™; Bluetooth®, or cellular communications for wireless communication, etc. The communication unit 1108 can link the processor(s) 1102 to a computer network that may in turn be coupled to other processing systems.

The display 1110 represents any device equipped to display electronic images and data as described herein. The display 1110 may be any of a conventional display device, monitor or screen, such as an organic light-emitting diode (OLED) display, a liquid crystal display (LCD). In some embodiments, the display 1110 is a touch-screen display capable of receiving input from one or more fingers of a user. For example, the device 1110 may be a capacitive touch-screen display capable of detecting and interpreting multiple points of contact with the display surface.

The input device(s) 1112 are any devices for inputting data on the computer system 1100. In some embodiments, an input device is a touch-screen display capable of receiving input from one or more fingers of the user. The functionality of the input device(s) 1112 and the display 1110 may be integrated, and a user of the computer system 1100 may interact with the system by contacting a surface of the display 1110 using one or more fingers. In other embodiments, an input device is a separate peripheral device or combination of devices. For example, the input device(s) 1112 may include a keyboard (e.g., a QWERTY keyboard) and a pointing device (e.g., a mouse or touchpad). The input device(s) 1112 may also include a microphone, a web camera, or other similar audio or video capture devices.

The data store 1114 can be an information source capable of storing and providing access to data. In the depicted embodiment, the data store 1114 is coupled for communication with the components 1102, 1104, 1108, 1110, and 1112 of the computer system 1100 via the bus 1116, and coupled, via the processor(s) 1102, for communication with the pathology visualizer 1105. In some embodiments, the pathology visualizer 1105 is configured to manipulate, i.e., store, query, update, and/or delete, data stored in the data store 1114 using programmatic operations.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

Furthermore, the description can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof. Furthermore, it should be understood that the modules, routines, features, attributes, methodologies and other aspects of the present subject matter can be implemented using hardware, firmware, software, or any combination of the three.

The invention claimed is:

1. A method for visualizing a pathology in an eye, said method comprising:
   collecting optical coherence tomography (OCT) image data of the eye from an OCT system;
   segmenting the OCT image data to identify two or more retinal layer boundaries located in the eye;
   selecting two retinal layer boundaries in the segmented OCT data;
   iteratively reshaping one of the layer boundaries relative to the other;
   generating an en face image for each iteration and analyzing the generated en face image; and
   stopping the iterative process when an en face image having a quality meeting predetermined criteria is generated; and
   displaying or storing the en face image having a quality meeting predetermined criteria or a further analysis thereof.

2. The method as recited in claim 1, wherein the pathology is choroidal neovascularization (CNV).

3. The method as recited in claim 1, wherein the predetermined criteria is based on one or more of contrast, brightness, background features suppressed, and noise signals removed.

4. The method as recited in claim 1, wherein the two or more retinal layer boundaries include the outer plexiform layer (OPL) and the retinal pigment epithelium (RPE).

5. The method as recited in claim 1, wherein the selection of the two or more retinal layer boundaries depends on an application and/or disease type associated with the pathology being visualized.

6. The method as recited in claim 1, wherein the en face image is further enhanced by suppressing its background features using a heat map, said heat map representing point-wise weight values for pixels in the image.

7. The method as recited in claim 6, wherein one or more point-wise weight values for one or more image pixels corresponding to the pathology is higher than the remaining pixels in the image.

* * * * *

UNITED STATES PATENT AND TRADEMARK OFFICE
CERTIFICATE OF CORRECTION

PATENT NO. : 10,832,402 B2  
APPLICATION NO. : 15/891965  
DATED : November 10, 2020  
INVENTOR(S) : Homayoun Bagherinia et al.

Page 1 of 1

It is certified that error appears in the above-identified patent and that said Letters Patent is hereby corrected as shown below:

In the Specification

In Column 1, Line 49, delete "PitfallsOCT" and insert -- Pitfalls OCT --, therefor.

In Column 6, Line 26, delete "$A_j(z)=|A_j|^{i\varphi}$." and insert -- $A_j(z)=|A_j|e^{i\varphi}$. --, therefor.

In Column 13, Line 47, delete "Zhang." and insert -- Zhang, --, therefor.

In Column 13, Line 51, delete "41:30-4143," and insert -- 4130-4143, --, therefor.

Signed and Sealed this  
Second Day of March, 2021

Drew Hirshfeld  
*Performing the Functions and Duties of the*  
*Under Secretary of Commerce for Intellectual Property and*  
*Director of the United States Patent and Trademark Office*